United States Patent [19]

Kuivila et al.

[11] Patent Number: 5,973,177
[45] Date of Patent: Oct. 26, 1999

[54] METHOD FOR SELECTING SILICON METALLOID HAVING IMPROVED PERFORMANCE IN THE DIRECT PROCESS FOR MAKING ORGANOHALOSILANES

[75] Inventors: Charles Spencer Kuivila, LaGrange, Ky.; David Clay Miller, Madison, Ind.

[73] Assignee: Dow Corning Corporation, Midland, Mich.

[21] Appl. No.: 09/123,972

[22] Filed: Jul. 29, 1998

[51] Int. Cl.⁶ .............................. C07F 7/16; C09K 3/00; C01B 33/00; C01B 33/02
[52] U.S. Cl. .............. 556/472; 252/182.32; 252/182.35; 423/111; 423/115; 423/324; 423/348
[58] Field of Search ............................ 556/472; 423/111, 423/115, 324, 348; 252/182.32, 182.35

[56] References Cited

U.S. PATENT DOCUMENTS

| | | | |
|---|---|---|---|
| 2,380,995 | 8/1945 | Rochow et al. | 260/607 |
| 2,380,996 | 8/1945 | Rochow et al. | 260/607 |
| 5,059,343 | 10/1991 | Halm et al. | 252/182.35 |
| 5,250,716 | 10/1993 | Mui | 556/472 |
| 5,312,948 | 5/1994 | Freeburne et al. | 566/472 |
| 5,427,952 | 6/1995 | Daugherty et al. | 436/72 |

OTHER PUBLICATIONS

Clark, J., Organometallic Chemistry, 376:165–222 (Apr. 1989).

*Primary Examiner*—Paul F. Shaver
*Attorney, Agent, or Firm*—William F. Boley

[57] ABSTRACT

A method for selecting chemical grade silicon metalloid having improved performance in a direct process for making organohalosilanes. The method comprises (A) heating a chemical grade silicon metalloid sample at a temperature ramp speed controlled to effect a stepwise reduction of oxide impurities present in the chemical grade silicon metalloid to a temperature greater than about 2300° C. in the presence of a carbon source thereby effecting the formation of a reduction product consisting of carbon monoxide and carbon dioxide, (B) determining the amount of the reduction product formed above a temperature of about 1900° C., and (C) selecting a chemical grade silicon metalloid for use in the direct process for making organohalosilanes based upon the amount of the reduction product formed above a temperature of about 1900° C.

9 Claims, No Drawings

METHOD FOR SELECTING SILICON METALLOID HAVING IMPROVED PERFORMANCE IN THE DIRECT PROCESS FOR MAKING ORGANOHALOSILANES

BACKGROUND OF INVENTION

The present invention is a method for selecting silicon metalloid having improved performance in a direct process for making organohalosilanes. The method comprises (A) heating a chemical grade silicon metalloid sample at a temperature ramp speed controlled to effect a stepwise reduction of oxide impurities present in the chemical grade silicon metalloid to a temperature greater than about 2300° C. in the presence of a carbon source thereby effecting the formation of a reduction product consisting of carbon monoxide and carbon dioxide, (B) determining the amount of the reduction product formed at above a temperature of about 1900° C., and (C) selecting a chemical grade silicon metalloid for use in the direct process for making organohalosilanes based upon the amount of the reduction product formed above a temperature of about 1900° C.

Organohalosilanes, particularly dialkyldichlorosilanes, are important intermediates in the silicone industry. The organohalosilanes are typically hydrolyzed and condensed to form polyorganosiloxanes which can then be processed to form, for example, silicone fluids, elastomers, sealants, adhesives, and resins. The predominant commercial process for preparing these organohalosilane intermediates is one commonly referred to as the "direct process," as originally described by Rochow, U.S. Pat. No. 2,380,995 issued Aug. 7, 1945, and Rochow et al., U.S. Pat. No. 2,380,996, issued Aug. 7, 1945.

Because of the high volume of organohalosilanes used in the silicone industry, considerable effort has been devoted to optimizing the conversion of the silicon metalloid to the diorganodihalosilane, particularly to dimethyldichlorosilane. It is known in the silicone industry that different lots of chemical grade silicon metalloid react differently in the direct process. To attempt to control the lot-to-lot variability of the reactivity of chemical grade silicon metalloid in the direct process, manufacturers of organohalosilanes have set strict controls on the acceptable types and levels of contaminants present in the silicon. Clarke, J., Organometallic Chemistry, 376:165–222 (1989) provides a comprehensive review of the direct process for synthesis of methylchlorosilanes and the effects of contaminants on the process.

Daugherty et al., U.S. Pat. No. 5,427,952, teach a method for analyzing chemical grade silicon intended for use in the direct process for the presence of contaminants, including oxides and carbides of calcium, aluminum, and silicon. The process involves the separation of the contaminants by an alloying process and subsequent analysis of the contaminants for chemical composition.

The present inventors have found that when chemical grade silicon metalloid is heated under controlled conditions to a temperature greater than about 2300° C. in the presence of a carbon source that a reduction product consisting of carbon monoxide and carbon dioxide which forms at above a temperature of about 1900° C. is predictive of the chemical grade silicon metalloid's performance in the direct process. The inventors have found that the smaller the amount of reduction product formed above a temperature of about 1900° C. the greater the specificity of the chemical grade silicon metalloid for the production of diorganodihalosilanes.

SUMMARY OF INVENTION

The present invention is a method for selecting chemical grade silicon metalloid having improved performance in a direct process for making organohalosilanes. The method comprises (A) heating a chemical grade silicon metalloid sample at a temperature ramp speed controlled to effect a stepwise reduction of oxide impurities present in the chemical grade silicon metalloid to a temperature greater than about 2300° C. in the presence of a carbon source thereby effecting the formation of a reduction product consisting of carbon monoxide and carbon dioxide, (B) determining the amount of the reduction product formed above a temperature of about 1900° C., and (C) selecting a chemical grade silicon metalloid for use in the direct process for making organohalosilanes based upon the amount of the reduction product formed above a temperature of about 1900° C.

DESCRIPTION OF INVENTION

The present invention is a method for selecting chemical grade silicon metalloid having improved performance in a direct process for making organohalosilanes. The method comprises (A) heating a chemical grade silicon metalloid sample at a temperature ramp speed controlled to effect a stepwise reduction of oxide impurities present in the chemical grade silicon metalloid to a temperature greater than about 2300° C. in the presence of a carbon source thereby effecting the formation of a reduction product consisting of carbon monoxide and carbon dioxide, (B) determining the amount of the reduction product formed at above a temperature of about 1900° C., and (C) selecting a chemical grade silicon metalloid for use in the direct process for making organohalosilanes based upon the amount of the reduction product formed above a temperature of about 1900° C.

The present method comprises a method for selecting a chemical grade silicon metalloid for use in a direct process for making organohalosilanes. By "chemical grade," it is meant any silicon metalloid comprising about 98 percent but less than 100 percent by weight silicon metalloid which typically may contain oxides of aluminum, calcium, and silicon as impurities, and which is useful in a direct process for making organohalosilanes.

By "direct process" for making organohalosilanes it is meant a process where an organohalide is reacted with silicon metalloid in the presence of a catalyst comprising copper at an elevated temperature to form a mixture comprising organohalosilanes.

The chemical grade silicon metalloid, hereinafter referred to in the alternative as "chemical grade silicon", is added preferably to the present method as a particulate. The method of forming the particulate chemical grade silicon is not critical to the present method and can be any of those known in the art for forming particulate chemical grade silicon, such as a ball mill. The size of the particulate chemical grade silicon is not critical to the present method since the chemical grade silicon is melted during conduct of the present method. Examples, but non-limiting, of sizes of particulate chemical grade silicon useful in the present invention are described in Freeburne et al., U.S. Pat. No. 5,312,948. Since the purpose of the present method is to select a chemical grade silicon for use in the direct process, it is preferred that the particulate chemical grade silicon be a representative sample of the bulk of particulate chemical grade silicon to be used in the direct process.

In the present method the chemical grade silicon is preferably heated under an inert atmosphere in the presence of a carbon source to effect a stepwise reduction of oxide impurities present in the chemical grade silicon. A result of this reduction is the formation of reduction product consisting of carbon dioxide and carbon monoxide. The means of heating the chemical grade silicon is not critical as long as the formation of carbon dioxide and carbon monoxide as a result of reducing oxide impurities present in the chemical grade silicon metalloid can be effectively monitored as a function of temperature. The inventors believe that the reduction product forming at above a temperature of about 1900° C. results from the carbothermic reduction of oxide impurities which are detrimental to the production of diorganodihalosilanes in the direct process.

Since chemical grade silicon can typically contain a number of oxide impurities such as oxides or silicates of aluminum and calcium, as well as silicon dioxide, it is important that the chemical grade silicon be heated at a controlled temperature ramp speed whereby reduction product peaks corresponding to different oxide impurities can be distinguished. The term "stepwise reduction" as used herein means that the temperature ramp speed is controlled such that the reduction product peaks corresponding to different oxide impurities can be distinguished. The inventors have unexpectedly found that the amount of reduction product formed at above a temperature of about 1900° C., corresponding to certain oxide or silicate impurities, is predictive of performance of chemical grade silicon in the direct process. The smaller the amount of reduction product formed at above a temperature of about 1900° C., the greater the specificity of the chemical grade silicon for the formation of diorganodihalosilanes. In a preferred process the heating is conducted in an electrical furnace under an inert atmosphere such as nitrogen or argon, with the temperature within the furnace being increased at a constant rate. The rate of increasing or ramping up the furnace temperature is not critical as long as distinct reduction product peaks corresponding to the different oxide impurities present in the chemical grade silicon are produced. Generally, it is preferred that the temperature ramp speed be less than about 20° C. per second. Most preferred is a temperature ramp speed within a range of about 5° C. to 10° C. per second. The heating can be effected in a commercially available oxygen analyzer, for example Leco Model RO-416DR, with a programmable temperature control function (Leco Corporation, St. Joseph, Mich.).

The present method requires a carbon source to effect the carbothermic reduction of the oxide impurities present in the chemical grade silicon. The carbon source is not critical to the present method and can be any such carbon source typically used in carbothermic reduction processes, such as graphite. In a preferred process the chemical grade silicon can be placed in, for example, a graphite crucible which can serve as the carbon source. The amount of the carbon source present in the method is not critical as long as sufficient carbon is available to effect carbothermic reduction of the oxide impurities present in the chemical grade silicon.

In the present method the oxide impurities present in the chemical grade silicon are reduced to form a reduction product consisting of carbon monoxide and carbon dioxide. In step (B) of the present method the amount of formation of this reduction product is determined as a function of temperature by any suitable means for determining such amount. The amount of reduction product can be determined by, for example, infrared spectroscopy, mass spectrometry, or thermal conductivity. In a preferred process the formation of the reduction products is measured by use of an oxygen analyzer using an infrared detector.

In step (C) of the present method the amount of reduction product formed above a temperature of about 1900° C. as determined in step (B) is used as a basis for selecting chemical grade silicon for use in a direct process for making organohalosilanes. The present inventors have found that the smaller the concentration of reduction product occurring above a temperature of about 1900° C., the greater the specificity of the chemical grade silicon for the production of diorganodihalosilanes in the direct process. Therefore, it is possible to screen different shipments or lots of chemical grade silicon and choose those lots or shipments having more or less specificity for diorganodihalosilane production, as may be required by commercial demand. The present method is especially suited for selecting chemical grade silicon for use in the direct process where the desired product is dimethyldichlorosilane.

The following example is provided to illustrate the present invention. The example is not intended to limit the scope of the claims herein.

EXAMPLE

A sample of a number of lots of chemical grade silicon were analyzed by the present method and the results correlated with the performance of the chemical grade silicon in a commercial direct process. For each sample, approximately 0.1 g of ground chemical grade silicon having an average particle size less than 100 mesh was weighed into a tin capsule and the capsule placed into a graphite crucible. The crucible was placed into a Leco Model RO-416DR oxygen analyzer (Leco Corporation, St. Joseph, Mich.) and heated in a controlled fashion to approximately 2600° C. at a rate of about 9° C. per second. The oxide impurities present in the samples were reduced and the carbon dioxide and carbon monoxide produced were measured by infrared absorbance as a function of time. A plot of relative oxygen concentration as a function of analysis time was made and demonstrated two oxygen peaks. The oxygen level (Wt. % Oxygen) associated with the peak formed above a temperature of about 1900° C. was quantified for each sample and is reported in Table 1. Each of the test lots were evaluated in a commercial direct process for producing methylchlorosilanes. Performance of the lots of chemical grade silicon in the direct process were calculated as % Yield= dimethyldichlorosilane selectivity (weight % of total product) x fractional silicon conversion. The results are summarized in Table 1 and illustrate the correlation between the amount of reduction product formed above about 1900° C. and the specificity of the chemical grade silicon for the formation of dimethyldichlorosilane.

TABLE 1

Correlation of Reduction Product With Direct Process Specificity for Dimethyldichlorosilane

| Sample No. | Wt. % Oxygen | % Yield $Me_2SiCl_2$ |
| --- | --- | --- |
| 1 | 0.048 | 86.4 |
| 2 | 0.076 | 86.6 |
| 3 | 0.034 | 85.0 |
| 4 | 0.060 | 84.9 |
| 5 | 0.049 | 85.1 |
| 6 | 0.091 | 84.3 |
| 7 | 0.122 | 82.1 |
| 8 | 0.177 | 81.9 |
| 9 | 0.140 | 80.8 |
| 10 | 0.165 | 80.9 |

We claim:

1. A method for selecting a chemical grade silicon metalloid having improved performance in a direct process for making organohalosilanes comprising (A) heating a chemical grade silicon metalloid sample at a temperature ramp speed controlled to effect a stepwise reduction of oxide impurities present in the chemical grade silicon metalloid to a temperature greater than about 2300° C. in the presence of a carbon source thereby effecting the formation of a reduction product consisting of carbon monoxide and carbon dioxide, (B) determining the amount of the reduction product formed at above a temperature of about 1900° C., and (C) selecting a chemical grade silicon metalloid for use in the direct process for making organohalosilanes based upon the amount of the reduction product formed above a temperature of about 1900° C.

2. A method according to claim 1, where the heating is conducted under an inert atmosphere.

3. A method according to claim 1, where the oxide impurities comprise oxides of aluminum.

4. A method according to claim 1, where the temperature ramp speed is less than about 20° C. per second.

5. A method according to claim 1, where the temperature ramp speed is within a range of about 5° C. to 10° C. per second.

6. A method according to claim 1, where the amount of reduction product is determined by use of an oxygen analyzer using an infrared detector.

7. A method according to claim 1, where the organohalosilanes comprise dimethyldichlorosilane and the chemical grade silicon is selected to favor formation of the dimethyldichlorosilane.

8. A method according to claim 1, where the carbon source is graphite.

9. A method for selecting a chemical grade silicon metalloid having improved specificity in a direct process for making dimethyldichlorosilane comprising (A) heating in an inert atmosphere a chemical grade silicon metalloid at a temperature ramp speed within a range of about 5° C. to 10° C. per second to effect a stepwise reduction of oxide impurities present in the chemical grade silicon metalloid to a temperature greater than about 2300° C. in the presence of a carbon source thereby effecting formation of a reduction product consisting of carbon monoxide and carbon dioxide, (B) determining the amount of the reduction product formed at above a temperature of about 1900° C. by means of an oxygen analyzer using an infrared detector, and (C) selecting a chemical grade silicon metalloid for use in the direct process for making dimethyldichlorosilane based upon the amount of the reduction product formed above a temperature of about 1900° C., where the smaller the amount of reduction product formed above a temperature of about 1900° C. the greater the specificity of the chemical grade silicon for the formation of dimethyldichlorosilane in the direct process.

* * * * *